(12) United States Patent
Larnard

(10) Patent No.: US 6,733,518 B2
(45) Date of Patent: May 11, 2004

(54) METHOD AND APPARATUS FOR THERMAL THERAPY

(75) Inventor: Donald J. Larnard, Hampton Falls, NH (US)

(73) Assignee: Seacoast Technologies, Inc., Portsmouth, NH (US)

( * ) Notice: Subject to any disclaimer, the term of this patent is extended or adjusted under 35 U.S.C. 154(b) by 0 days.

(21) Appl. No.: 10/274,757

(22) Filed: Oct. 21, 2002

(65) Prior Publication Data

US 2003/0083721 A1 May 1, 2003

Related U.S. Application Data

(60) Provisional application No. 60/334,740, filed on Oct. 31, 2001.

(51) Int. Cl.⁷ .................................................. A61F 7/00
(52) U.S. Cl. ...................... 607/105; 607/104; 607/113
(58) Field of Search ......................... 604/890.1; 607/96, 607/104–106, 113

(56) References Cited

U.S. PATENT DOCUMENTS

| | | | | |
|---|---|---|---|---|
| 3,797,485 A | * | 3/1974 | Urquhart | 604/288.04 |
| 4,256,094 A | * | 3/1981 | Kapp et al. | 601/152 |
| 4,423,725 A | | 1/1984 | Baran et al. | |
| 5,150,706 A | | 9/1992 | Cox et al. | |
| 6,132,419 A | | 10/2000 | Hofmann | |
| 6,306,130 B1 | * | 10/2001 | Anderson et al. | 606/27 |
| 6,325,818 B1 | | 12/2001 | Werneth | |

* cited by examiner

Primary Examiner—Roy D. Gibson
(74) Attorney, Agent, or Firm—Christopher & Weisberg, P.A.

(57) ABSTRACT

A medical device for controlling the temperature of a region of brain tissue. Selective cooling of the brain is achieved by lowering the localized blood temperature of the internal blood vessel. The medical device controls the localized temperature of the brain by cradling the blood vessel and transferring thermal energy between the medical device and the blood vessel.

20 Claims, 6 Drawing Sheets

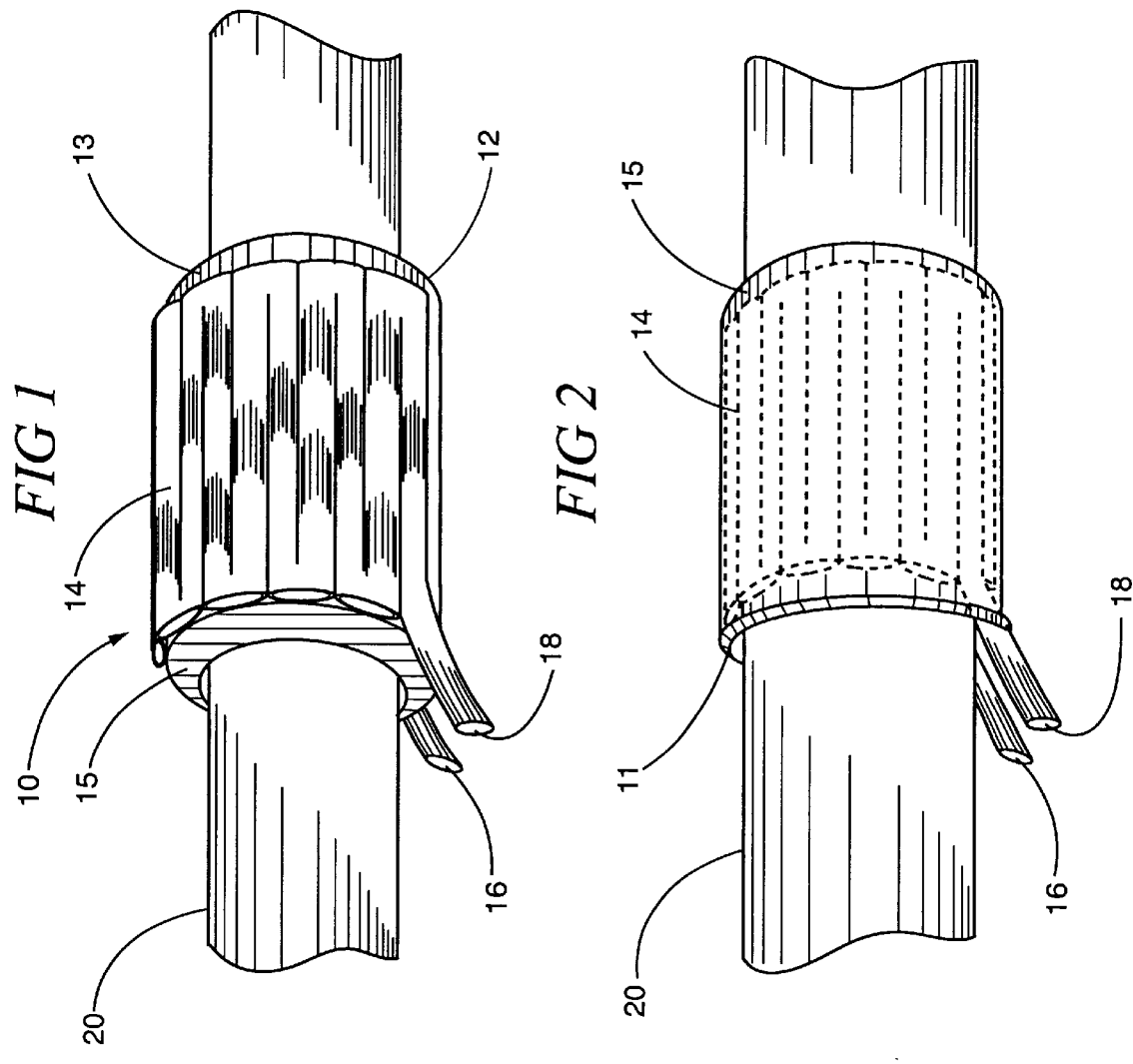

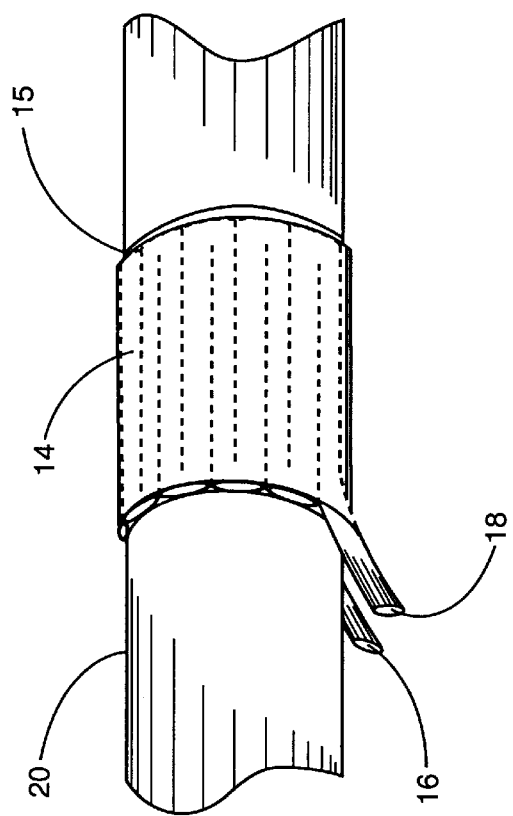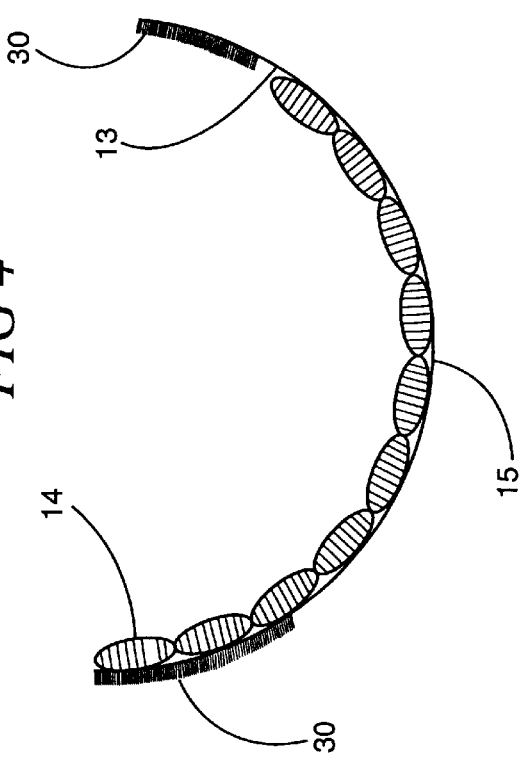

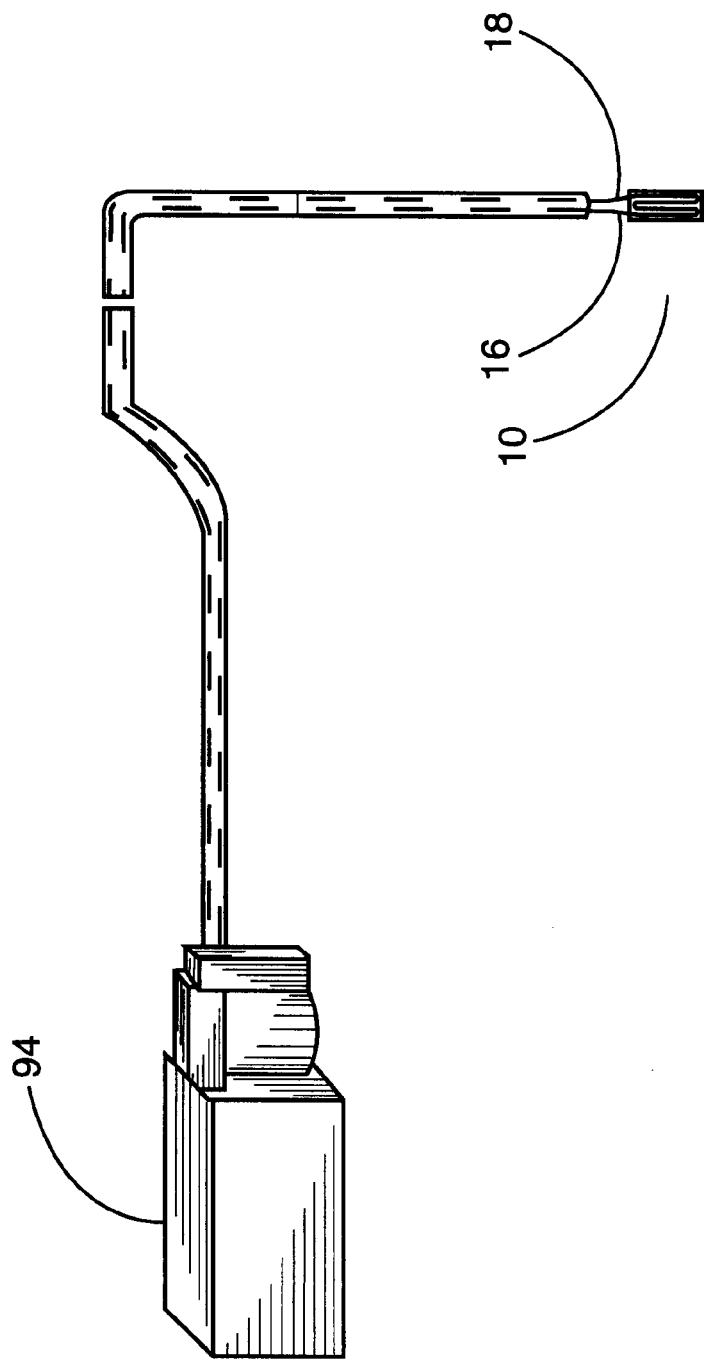

METHOD AND APPARATUS FOR THERMAL THERAPY

CROSS-REFERENCE TO RELATED APPLICATION

This application is related to and claims priority to U.S. Provisional Patent Application Serial No. 60/334,740, filed Oct. 31, 2001, entitled METHOD AND APPARATUS FOR THERMAL THERAPY, the entirety of which is incorporated herein by reference.

STATEMENT REGARDING FEDERALLY SPONSORED RESEARCH OR DEVELOPMENT n/a

FIELD OF THE INVENTION

The subject invention relates to a system and method for controlling the temperature of a region of brain tissue.

BACKGROUND OF THE INVENTION

Researchers and physicians have long recognized the consequences of reduction of body temperature in mammals, including induction of stupor, tissue damage, and death. Application of freezing and near freezing temperatures to selected tissue is commonly employed to preserve tissue and cell (e.g. sperm banks); and application of extreme cold (far below freezing) is effective for tissue ablation. However, localized cooling (not freezing) of tissue has generally been limited to the placement of an "ice-pack" or a "cold compress" on injured or inflamed tissue to reduce swelling and the pain associated therewith. Localized cooling of internal organs, such as the brain, has remained in large part unexplored.

For example, "brain cooling" has been induced by cooling the blood supply to the brain by inserting a chilled catheter into the arteries. However, as the effects of the cold blood cannot be easily localized, the shortcomings of systemically cooling the entire blood pool are realized, and the technique become impractical. Such shortcomings include cardiac arrhythmia, immune suppression and coagulopathies.

Attempts have been made to localize cooling of the brain with wholly external devices, such as cooling helmets or neck collars. Cooling helmets appear to be ineffective at reaching depths within the brain due to insufficient cooling power. Neck collars attempt to cool blood supplies and therefore become a systemic blood cooling method and thus are subject to the same shortcomings as other systemic cooling methods.

It is therefore desirable to obtain improved devices and methods that allow for localized brain cooling without the disadvantages of the known systemic and external devices and techniques.

SUMMARY OF THE INVENTION

The subject invention advantageously provides a system and method for controlling the temperature of a blood vessel. As described herein, the device lowers the localized blood temperature of the blood vessel by enveloping the blood vessel to transfer thermal energy there between. In this manner the device can, for example, lower the localized blood temperature of the internal carotid artery to affect selective cooling of the brain.

The medical device of the subject invention controls the localized temperature of the blood vessel by surrounding the blood vessel and transferring thermal energy between the medical device and the blood vessel. The medical device includes a thermal support structure for surrounding the blood vessel, whereby the support structure is configured to control thermal energy transfer between the support structure and the blood vessel. In exemplary usage, the temperature is controlled using thermally-conductive fluid perfusion through the thermal structure surrounding an outside section of blood vessel.

In a method of use, the medical device is placed using a cut-down procedure, either sliding or placing the device under the dissected blood vessel and securing. In this way, one avoids any adjacent nerves, and assures that other peripheral or peri-vascular structures are insulated. Once secured, the thermally-conductive fluid enters the thermal transfer region, thereby effecting the localized blood temperature of the blood vessel. For example, the localized temperature of the blood vessel is lowered by a perfusion of thermally-conductive fluid having a temperature lower then that of the blood vessel. Alternatively, the localized temperature of the blood vessel is increased by a perfusion of thermally-conductive fluid having a temperature greater then that of the blood vessel.

BRIEF DESCRIPTION OF THE DRAWINGS

A more complete understanding of the subject invention, and the attendant advantages and features thereof, will be more readily understood by reference to the following detailed description when considered in conjunction with the accompanying drawings wherein:

FIG. 1 shows a perspective view of a flexible thermal support structure embodiment the subject invention secured about the blood vessel;

FIG. 2 shows a perspective view of an alternative flexible thermal support structure embodiment of the subject invention secured about the blood vessel;

FIG. 3 shows a perspective view of a still further flexible thermal support structure embodiment of the subject invention secured about the blood vessel;

FIG. 4 shows a front view of a flexible thermal support structure of the subject invention;

FIG. 10 is a view of an exemplary system in a bundled state.

DETAILED DESCRIPTION OF THE INVENTION

Figure 5:
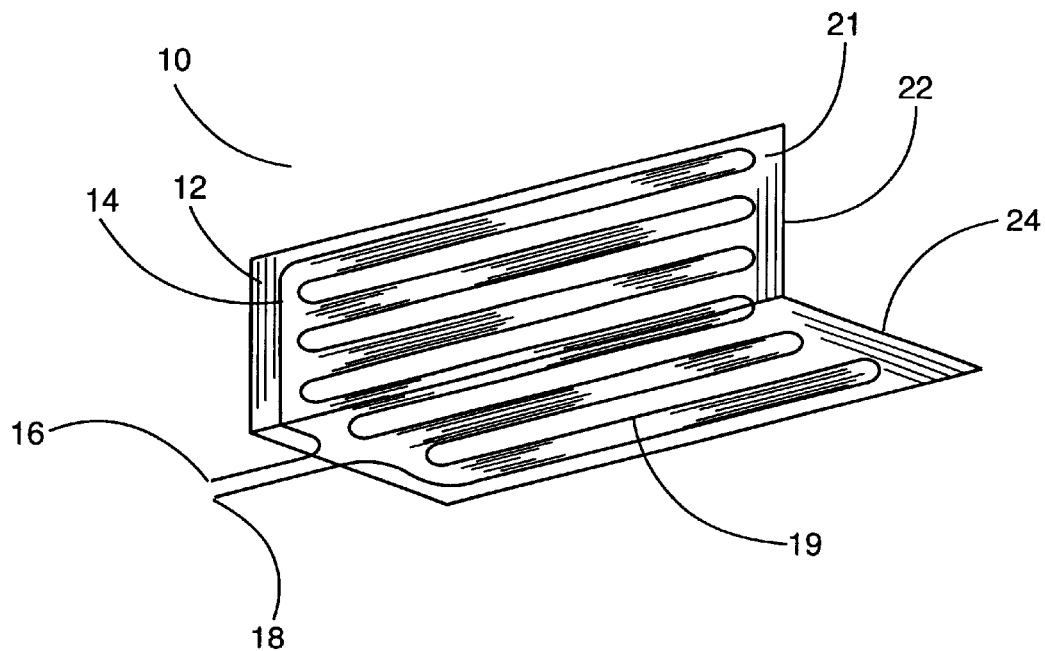
FIG. 5 shows a perspective view of a substantially rigid two element embodiment of the subject invention.

The subject invention provides a device for controlling the temperature of a blood vessel. As described herein, the device lowers the localized blood temperature of the blood vessel by enveloping the blood vessel and transferring thermal energy there between. In this manner, the device can, for example, effect a selective cooling of the brain or other body organ or organ system.

Referring now to FIG. 1, the medical device 10 includes a thermal support structure 12 for enveloping the blood vessel 20, whereby the thermal support structure 12 is configured to control thermal energy transfer between the thermal support structure 12 and the blood vessel 20. In exemplary usage, the temperature is controlled using thermally-conductive fluid perfusion through the thermal structure surrounding an outside section of the blood vessel. The thermally-conductive fluid lowers the localized blood temperature of the blood vessel, thereby effecting a selective temperature change.

In an embodiment, the thermal support structure 12 is a substantially flexible support structure 15, where the flexible support structure 15 is circumferentially wrapped about the blood vessel 20. The length of blood vessel circumferentially wrapped can be any length exposed by the cut down procedure and required by the flow of the vessel and the resting temperature of the blood to sufficiently cool the downstream tissue. The flexible support structure 15 can be made from, but not limited to, flexible materials including rubber, silastic or silicone.

As shown in FIG. 4, the flexible support structure 15 is secured about the blood vessel by, for example, the use of a hook and loop type fastener. Alternatively, the flexible support structure 15 can be fastened to itself by various other means including securing with a suture, piece of tape, or other securing method known in the art.

In an embodiment, a fluid conduit 14 is affixed to the exterior surface 13 of the flexible support structure 15. The fluid conduit 14 contains a fluid inlet 16 and fluid outlet 18 defining a fluid path through the fluid conduit 14. The fluid conduit 14 is orientated to create a thermal transfer region 19 on the flexible support structure 15, whereby the thermal transfer region 19 is in thermal communication with the blood vessel 20.

In an embodiment, the fluid conduit is flexible tubing, such as, but not limited to, silicone tubes, PET or Teflon tubing.

In an alternative embodiment, as shown in FIG. 2, the fluid conduit 14 is affixed to the interior surface 11 of flexible support structure 15. As such, the flexible support structure 15 acts as thermal barrier protecting the adjacent nerves and tissues from thermal damage.

In a further embodiment, as shown in FIG. 3, the fluid conduit 14 is integrated into the flexible support structure 15.

In an alternative embodiment as shown in FIG. 5, the thermal support structure 12 is made up of substantially rigid side elements 22 and 24, where the side elements 22 and 24 are configured to at least partially surround the blood vessel 20. As shown in FIG. 5, in an exemplary embodiment, the thermal support structure 12 includes two side elements 22 and 24, where the side elements 22 and 24 are affixed in substantial perpendicular relation. The fluid conduit 14 is affixed to the side elements 22 and 24 and orientated to create a thermal transfer region 19, whereby the thermal transfer region 19 is in thermal communication with the blood vessel 20.

In an embodiment, a fluid conduit 14 is affixed to the interior surface 21 of the side elements 22 and 24. As such, the side elements 22 and 24 act as thermal barrier protecting the adjacent nerves and tissues from thermal damage. The fluid conduit 14 contains a fluid inlet 16 and fluid outlet 18 defining a fluid path through the fluid conduit 14. The fluid conduit 14 is orientated to create a thermal transfer region 19 on the side elements 22, whereby the thermal transfer region 19 is in thermal communication with the blood vessel 20.

In an alternative embodiment, not shown, the fluid conduit 14 is affixed to the exterior surface of the side elements 22 and 24.

In a further embodiment, not shown, the fluid conduit 14 is integrated into the side elements 22 and 24.

Figure 6:
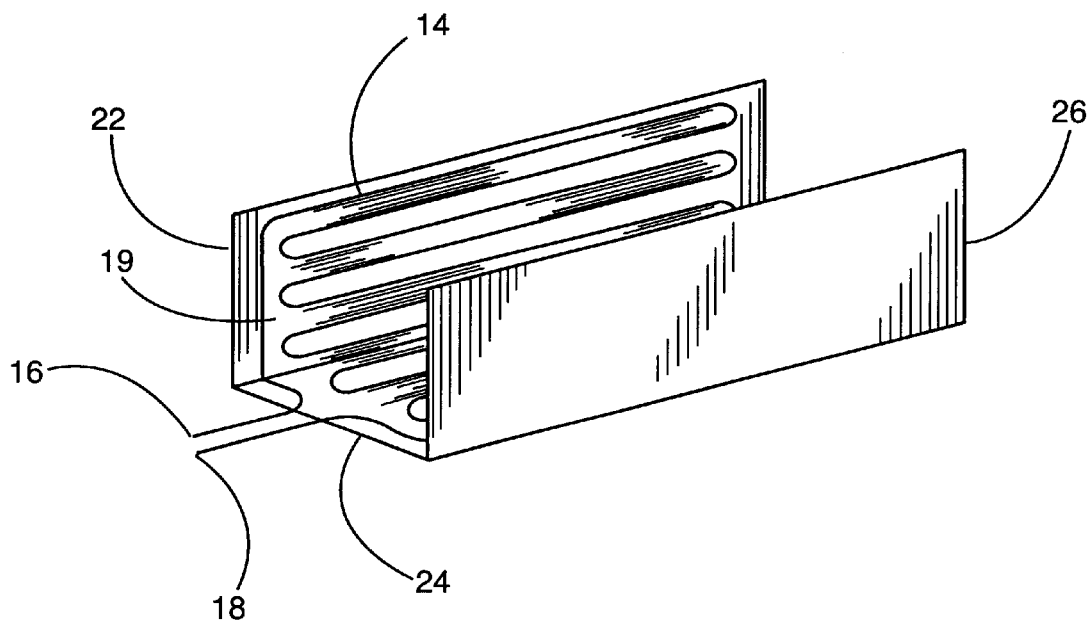
FIG. 6 shows a perspective view of a substantially rigid three element embodiment of the subject invention.

In an alternative embodiment, as shown in FIG. 6, the support structure 12 includes three side elements 22, 24 and 26 where the side elements 22, 24 and 26 are affixed together forming an open channel, having a pair of substantially parallel vertical elements 22 and a horizontal element 24. The fluid conduit 14 is affixed to the vertical elements 22 and 26 and a horizontal element 24, orientated to create a thermal transfer region 19, whereby the thermal transfer region 19 is in thermal communication with the blood vessel 20.

Figure 7:
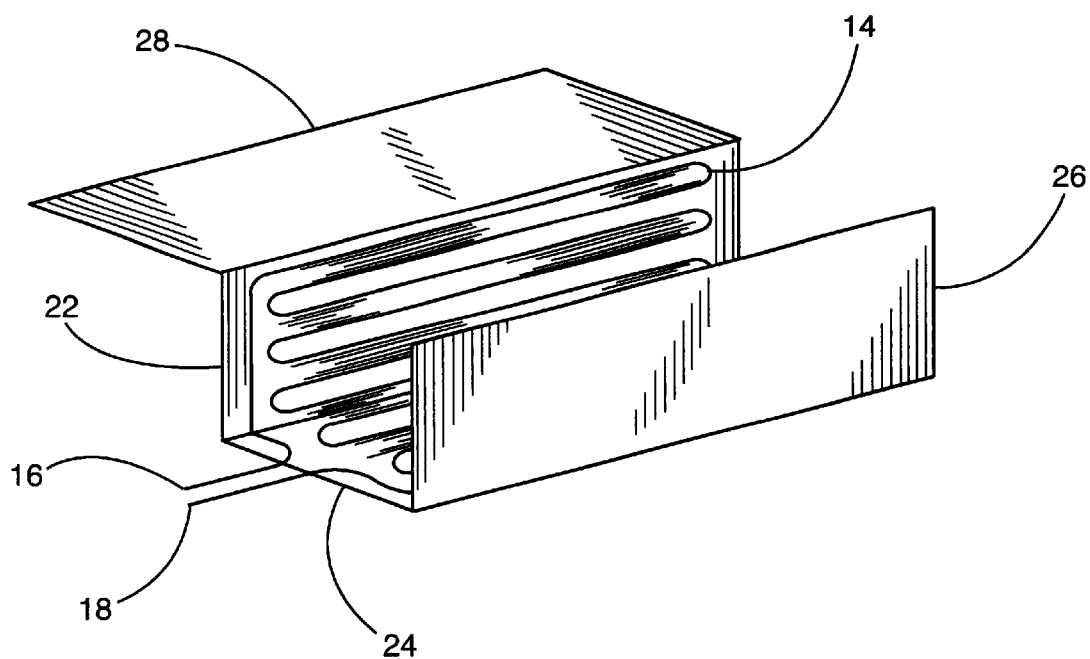
FIG. 7 shows a perspective view of a substantially rigid four element embodiment of the subject invention.

In an embodiment as shown in FIG. 7, the support structure further includes a cover 28, whereby the cover is hingeably connected to a first vertical side element 22. The cover 28 is rotated over the blood vessel 20 contacting the opposing vertical side element 26.

The side elements 22, 24 and 26 can be made from an insulating material, such as, plastic or rubber, where the insulating material insulates the adjacent tissue and nerves from thermal damage.

Figure 8:
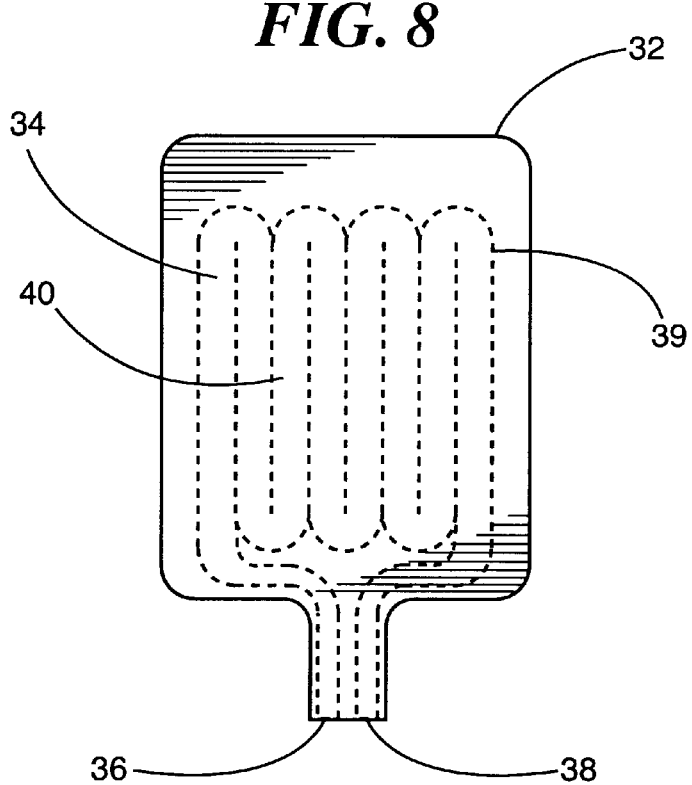
FIG. 8 show a continuous bag thermal support structure embodiment of the subject invention.

In an alternative embodiment, as shown in FIG. 8, the thermal support element 12 can be a continuous bag 32 or polymer sac, where portions of the bag 32 are selectively sealed to define a fluid path 34 therethrough. The fluid path 34 is oriented such that the bag 32 contains a fluid inlet 36 and fluid outlet 38 and creates a thermal transfer region 40, whereby the thermal transfer region 40 is in thermal communication with the blood vessel 20 or internal organ or organ system.

Figure 9:
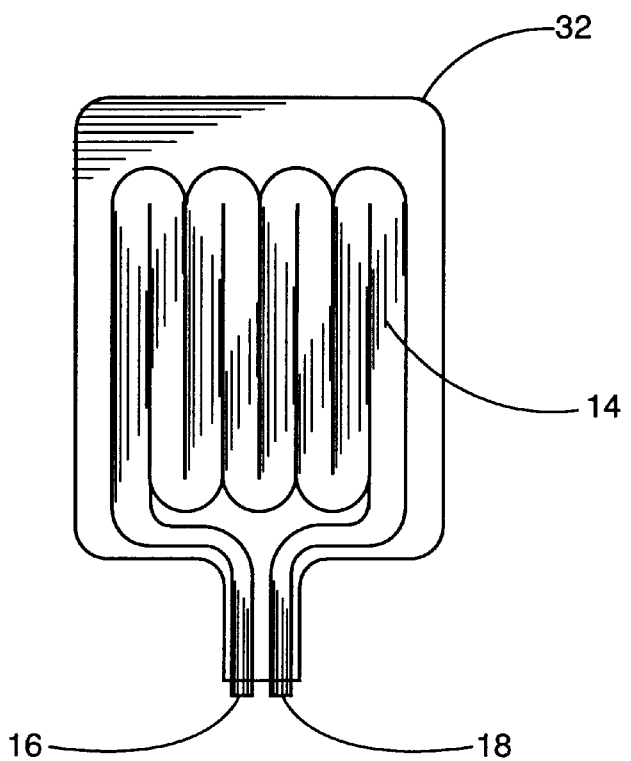
FIG. 9 show an alternative continuous bag thermal support structure embodiment of the subject invention.

In alternative embodiment, as shown in FIG. 9, the continuous bag 32 includes a fluid conduit 14 positioned within the bag 32. The fluid conduit 14 contains a fluid inlet 16 and fluid outlet 18 defining a fluid path through the fluid conduit 14. The fluid conduit 14 is orientated to create a thermal transfer region 19 in the continuous bag 32, whereby the thermal transfer region 19 is in thermal communication with the blood vessel 20 or internal organ or organ system.

The continuous bag 32 can be secured about the blood vessel 20, internal organ or organ system by various means, including, but not limited to, securing with the use of a hook and loop type fastener, a suture, a piece of tape, or other securing methods known in the art.

In an exemplary system, as shown in FIG. 10, the fluid inlet 16 is in fluid communication with a thermally-conductive fluid source 94 and the fluid outlet 18 is in fluid communication with the thermally-conductive fluid source 94 such that a fluid circulation circuit is defined. In practice, once the thermal support structure 12 is position and secured about the blood vessel 20, the thermal transfer region 19 being in thermal communication with the blood vessel 20, the thermally-conductive fluid enters the thermal transfer region 19, through the fluid inlet 16, thermally affecting the blood vessel 20. Simultaneously, the fluid outlet 18 excavates the thermally-conductive fluid from the thermal transfer region 19. In this manner, the thermal transfer region 19 affects a specific controlled temperature to the blood vessel 20.

The thermally-conductive fluid can be water, saline, a mixed fluorocarbon solution, or a refrigerant which is cooled by a thermoelectric cooler or a refrigerant fluid. The mixed fluorocarbon solution may be compounded such that it is deployed in liquid form wherein the liquid undergoes a phase change and transforms to a gas at a tailored boiling point.

In an embodiment, not shown, the thermally-conductive fluid source 94 can be responsive to input from a user input device to permit flow of the thermally-conductive fluid into the thermal transfer region 19. One or more temperature sensors in electrical communication with the thermally-conductive fluid source 94 can be provided to regulate or terminate the flow of thermally-conductive fluid into the thermal transfer region 19 when a predetermined temperature at a selected point or points on or within the thermal transfer region 19 is/are obtained.

In an exemplary method of use, the medical device is placed using a cut-down procedure, either sliding or placing the device under the dissected blood vessel and securing. In this way, any adjacent nerves or vascular structures are insulated to avoid thermal damage. Once secured, the thermally-conductive fluid enters the thermal transfer region 19, through the fluid inlet 16, thermally affecting the blood vessel 20, thereby affecting the localized blood temperature of the blood vessel to effect selective temperature change. The selective temperature range achieved in the blood can be any temperature between zero degrees Celsius and normal blood temperature of 37 degrees Celsius. The temperature of the circulating fluid entering the thermal transfer region can be any temperature needed to reach the selective temperature range in the blood.

In an embodiment, of a method of use, the temperature of the thermally-conductive fluid entering the thermal transfer region is less than the temperature of the blood vessel. As such, the thermally-conductive fluid has a cooling effect on the blood vessel, thereby lowering the localized blood temperature of the blood vessel to effect selective cooling.

In an additional embodiment of a method of use, the temperature of the thermally-conductive fluid entering the thermal transfer region is greater than the temperature of the blood vessel. As such, the thermally-conductive fluid has a warming effect on the blood vessel, thereby increasing the localized blood temperature of the blood vessel to effect selective warming.

In an exemplary method of use, the medical device is placed using a cut-down procedure, either sliding or placing the device under the dissected internal carotid artery and securing. In this way, one could avoid any peripheral or cranial nerves, assure that other peripheral or peri-vascular structures are insulated and avoid the carotid bulb area at the bifurcation. Once secured, the thermally-conductive fluid enters the thermal transfer region 19, through the fluid inlet 16, thermally affecting the carotid artery.

For example, the temperature of the thermally-conductive fluid is lower than the temperature of the carotid artery, thereby lowering the localized blood temperature of the internal carotid artery to effect selective cooling of the brain.

It will be appreciated by persons skilled in the art that the subject invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    a thermal transfer structure adapted to envelop at least a portion of a blood vessel; and
    a thermally-conductive fluid in fluid communication with the thermal transfer structure.

2. A medical device comprising:
    a thermal transfer structure adapted to envelop at least a portion of a blood vessel, the thermal transfer structure including:
        a thermal support structure; and
        a thermal transfer region including a fluid inlet and a fluid outlet defining a fluid path through the thermal transfer region,
    wherein the thermal transfer region is affixed to the thermal support structure.

3. The medical device according to claim 2, wherein the thermal transfer region is affixed to an interior surface of the thermal support structure.

4. The medical device according to claim 2, wherein the thermal transfer region is affixed to an exterior surface of the thermal support structure.

5. The medical device according to claim 2, wherein the thermal transfer region is integrated into the thermal support structure.

6. The medical device according to claim 2, wherein the thermal support structure comprises a plurality of substantially rigid side elements.

7. The medical device according to claim 2, wherein the thermal support structure comprises at least two substantially rigid side elements.

8. The medical device according to claim 2, wherein the thermal support structure comprises at least three substantially rigid side elements.

9. The medical device according to claim 8, wherein the thermal support structure further comprises a cover element.

10. The medical device according to claim 2, wherein the thermal support structure is a flexible membrane, wherein the flexible membrane at least partially envelops the blood vessel.

11. The medical device according to claim 2, wherein the thermal support structure is a continuous bag, wherein the continuous bag at least partially envelops the blood vessel.

12. The medical device according to claim 11, wherein the thermal transfer region is integrated into the continuous bag.

13. The medical device according to claim 2, wherein the thermal support structure includes a means for securing the thermal support structure about the blood vessel.

14. A medical device for affecting a localized temperature of a blood vessel comprising:
    a thermal support structure; and
    a fluid conduit containing a fluid inlet and a fluid outlet defining a fluid path through the fluid conduit, the fluid conduit being shaped forming a fluid transfer region,
    wherein the fluid conduit is affixed to the thermal support structure.

15. A medical device for controlling the temperature of a blood vessel comprising:
    a thermal support structure configured to surround at least a portion of the blood vessel;
    a thermal transfer region attached to the thermal support structure, wherein the thermal transfer region is in thermal relation with the blood vessel; and
    a supply of thermally-conductive fluid in fluid communication with the thermal transfer region.

16. A method for effecting a temperature of a blood vessel comprising the steps of:
    providing a thermal transfer structure configured to control thermal energy transfer between the thermal transfer structure and the blood vessel;
    exposing a portion of the blood vessel;
    placing the thermal transfer structure about a portion of the blood vessel, such that the thermal support structure envelops at least a portion of the blood vessel; and
    creating a temperature differential between the blood vessel and the thermal support structure, such that thermal energy is transferred between the blood vessel and the thermal support structure.

17. The method of according to claim 16, wherein the thermal support structure is in fluid communication with a thermally-conductive fluid.

18. The method according to claim 17, where in a temperature of the thermo-conductive fluid is greater than the temperature of the blood vessel.

19. The method according to claim 17, where in a temperature of the thermo-conductive fluid is less than the temperature of the blood vessel.

20. A method of using a medical device for effecting a temperature of a blood comprising the steps of:

provided the thermal transfer structure including a thermal support structure configured to surround at least a portion of the blood vessel, a thermal transfer region attached to the thermal support structure, and a supply of thermally-conductive fluid in fluid communication with the thermal transfer region;

exposing at least a portion of the blood vessel;

securing the thermal transfer structure about a portion of the blood vessel, such that the thermal transfer region is in thermal communication with the blood vessel; and transferring the thermally-conductive fluid through the thermal transfer region to create a temperature differential between the blood vessel and the thermal transfer region, such that thermal energy is transferred between the blood vessel and the thermal transfer region.

* * * * *